United States Patent [19]
Dowdle

[11] Patent Number: 6,001,355
[45] Date of Patent: Dec. 14, 1999

[54] PRO-TPA FOR THE TREATMENT OF THROMBOSIS, EMBOLISM AND RELATED CONDITIONS

[76] Inventor: Eugene Bernard Davey Dowdle, Annalong, 1 Norwich Drive, Bishopscourt, Cape Town, South Africa, 7700

[21] Appl. No.: 07/890,335

[22] Filed: May 26, 1992

Related U.S. Application Data

[63] Continuation of application No. 07/150,475, Jan. 28, 1988, abandoned, which is a continuation of application No. 06/843,405, Mar. 24, 1986, abandoned, which is a continuation of application No. 06/559,569, Dec. 8, 1983, abandoned, which is a continuation-in-part of application No. 06/513,145, Jul. 12, 1983, abandoned.

[30] Foreign Application Priority Data

Dec. 24, 1982 [ZA] South Africa ............................ 82/9168
Jan. 11, 1983 [AU] Australia ................................ 10296/83

[51] Int. Cl.$^6$ .......................... A61K 38/48; A61K 38/49; C12N 9/48; C12N 9/64
[52] U.S. Cl. .................................. 424/94.64; 424/94.63; 435/212
[58] Field of Search ................................ 424/94.61, 212, 424/214, 215, 216, 217, 94.64, 94.63; 435/212

[56] References Cited

U.S. PATENT DOCUMENTS

| | | | |
|---|---|---|---|
| 4,165,258 | 8/1979 | Pye et al. | 435/215 |
| 4,245,051 | 1/1981 | Reich et al. | 435/212 |
| 4,552,760 | 11/1985 | Murakami et al. | 424/94.1 |
| 4,898,825 | 2/1990 | Morii et al. | 435/212 |
| 4,960,702 | 10/1990 | Rice et al. | 424/94.64 |
| 4,978,620 | 12/1990 | Morii et al. | 435/212 |
| 5,288,490 | 2/1994 | Budzynski et al. | 424/94.64 |
| 5,316,766 | 5/1994 | Baldus et al. | 424/94.63 |
| 5,496,549 | 3/1996 | Yamazaki et al. | 424/158.1 |

FOREIGN PATENT DOCUMENTS

| | | |
|---|---|---|
| 0041766 | 12/1981 | European Pat. Off. . |
| 100982 | 2/1984 | European Pat. Off. . |
| 112122 | 4/1984 | European Pat. Off. . |
| 0112122 | 8/1991 | European Pat. Off. . |

OTHER PUBLICATIONS

Granelli–Piperno et al., J. Exp. Med., 148(1), "A Study of Proteases and Protease–Inhibitor Complexes in Biological Fluids", pp. 223–234, Jul. 1978.

Binder et al., J. Biol. Chem., 254(6), "Purification and Characterization of Human Vascular Plasminogen Activator Derived from Blood Vessel Perfusates", pp. 1998–2003, Mar. 1979.

Heussen, C. An inhibitor of Tissue Plasminogen Activator Isolated from the Seeds of the South African Tree, *Erythrina latissima*, $6^{th}$ Int. Congress of Fibrinolysis, Lausanne, Switzerland Jul. 20–23, 1982 Haimostasis 1 (Suppl 1) 1982.42.

Heussen et al., "Purification of Human Tissue Plasminogen Activator with *Erythrina trypsin* Inhibitor", *J. Biol. Chem.* vol. 259, No. 19, Oct. 10, 1984; pp. 11,635–11,638.

Heussen et al., "An Inhibitor of Tissue Plasminogen Activator Isolated from the Seeds of the South African Tree, *Erythrina latissima*",; $6^{th}$ International Congress of Fribinolysis, Lausanne, Switzerland, Jul. 20–23, 1982. *Haemostascis* 11 (Suppl. 1), 1982, p. 47.

Rijken et al., "Fibrinolytic Properties of One–Chain and Two–Chain Human Extrinsic (Tissue–type) Plasminogen Activator", *J. Biol. Chem.*, vol. 257, No. 6, Mar. 25, 1982; pp. 2920–2925.

Collen, D., "Synergism of Tissue–type Plasminogen . . . this Effect", *Thrombosis and Haemostasis*, vol. 37(3), p. 373, 1987.

*Primary Examiner*—Jon P. Weber
*Attorney, Agent, or Firm*—Millen, White, Zelano, & Branigan, P.C.

[57] ABSTRACT

Pro-tPA has a higher affinity for fibrin and better selectivity than tPA and is used for the management and prophylaxis of thrombosis, embolism, and related conditions. A pharmaceutical composition comprises a physiological compatible medium and pro-tPA employed in a couple of 70–100% pro-tPA and 0–30% of tPA.

23 Claims, No Drawings

PRO-TPA FOR THE TREATMENT OF THROMBOSIS, EMBOLISM AND RELATED CONDITIONS

This application is a continuation of Ser. No. 07/150,475, filed Jan. 28, 1988, now abandoned, which is a continuation of Ser. No. 06/843,405, filed Mar. 14, 1986, now abandoned, which is a continuation of Ser. No. 06/559,569, filed Dec. 8, 1983, now abandoned, which is a continuation in part of Ser. No. 06/513,145, filed Jul. 12, 1983, now abandoned.

INTRODUCTION

The present invention relates to a process for selectively and reversibly adsorbing tissue plasminogen activator and/or its precursor from aqueous media containing it, in particular, for preparing plasminogen activators, namely, tPA and/or its precursor and/or urokinase in purified form, to a novel affinity reagent for tissue plasminogen activator and its precursor required for the process and to pharmaceutical and/or fibrinolytic preparations comprising the plasminogen activator prepared by the process and/or comprising the precursor as obtained by the process.

BACKGROUND OF THE INVENTION tPA is the abbreviation adopted in the art for a tissue plasminogen activator, i.e., the 2-chain type of plasminogen activator which has been identified for example in Bowes melanoma cells. Pro-tPA is the abbreviated name given to the precursor of tPA, i.e., a single chain compound having the same molecular weight as tPA and which by certain enzymes is converted into double chain tPA. According to the prior art literature, the single- and double-chain forms were said to both have virtually identical activity. The present invention will be shown to involve a radical departure from that view.

Plasminogen activators are substances which by their action upon plasminogen (a precursor of plasmin) result in the formation of plasmin. Plasmin in turn acts upon fibrin (or blood clots) to liquefy or dissolve the fibrin. Plasmin also causes lysis of fibrinogen which is a precursor of fibrin.

The aforegoing effects play an important role in the natural fibrinolytic systems. They are also put to use in the therapeutic administration of plasminogen activators for the management of thrombotic disease or other conditions where it is desirable to produce local fibrinolytic or proteolytic activity via the mechanism of plasminogen activation.

They may also find use in reagents for diagnostic, pathological or scientific tests involving fibrinolysis in vitro.

Two activators of human plasminogen are extensively used. The first of these is the bacterial protein, streptokinase, which functions by a non-proteolytic mechanism. The second is the protease, urokinase, which is obtained from urine or cultured kidney cells, although it is also known to occur in most other kinds of mammalian tissue. These two compounds have the therapeutic disadvantage that their action is not confined to plasminogen associated with fibrin in blood clots. They act upon plasminogen generally in the circulation and, in consequence, produce widespread plasmin generation with extensive lysis of fibrinogen, the precursor of fibrin. This may in turn lead to a bleeding state as a result of ineffective normal coagulation of the blood. Furthermore, urokinase has had the disadvantage that it is costly to isolate and prepare and is obtained in poor yields by the processes currently in use. This disadvantage also applies to valuable uses of urokinase other than fibrinolytic therapy, and restricts the availability of urokinase as a valuable commercial product for such uses. Streptokinase, being a foreign protein, elicits an immune response from the patient. The resulting antibodies neutralise the action of streptokinase on plasminogen and hence diminish its therapeutic efficacy.

A third plasminogen activator referred to generally as "tissue plasminogen activator" hereinafter referred to as "tPA" is also known to exist. This enzyme is found in most human tissues and is identical to or indistinguishable from an enzyme that is also a characteristic secretory product of human melanoma cells cultured in vitro. Although it catalyzes the proteolytic activation of plasminogen in much the same way as does urokinase, tPA differs from urokinase in a number of important respects. The two enzymes are chemically dissimilar. They have different molecular weights and each fails to react with antibodies to the other enzyme. The catalytic action of tPA is enhanced by fibrin whereas that of urokinase is not. tPA has the important property that it binds to fibrin, whereas urokinase fails to do so. These facts are recorded in a recent article entitled "Purification and characterisation of the plasminogen activator secreted by human melanoma cells in culture" by C Dingeman C. Rijken et alia (J. of Biological Chem., 256, No 13, pages 7035 to 7041). That same article also describes the preparation of tPA from a cultured human melanoma cell line as well as from normal human tissue. The purification procedure consisted of successive chromatography on zinc chelate-agarose, concanavalin A-agarose and sephadex G-150 in the presence of detergent.

The tendency for tPA to bind to fibrin, its greatly enhanced fibrinolytic action in the presence of fibrin and when compared to urokinase and streptokinase, its relatively inefficient function as a plasminogen activator in the absence of fibrin combine to make tPA a plasminogen activator of choice for human thrombolytic therapy. Interactions between fibrin and tPA to a considerable extent localise the plasmin generation to the site of the clot and mitigate or avoid the consequences of promiscuous plasminogen activation as observed when urokinase or streptokinase is used. Furthermore streptokinase is a protein which is immunochemically foreign to man, whereas tPA is not.

A recent report entitled "Specific lysis of an iliofemoral thrombis by administration of extrinsic (tissue type) plasminogen activator" by W. Weimar et alia (Lancet, Nov. 7, 1981, page 1018) testifies to the clinical usefulness of tPA in the management of human thrombotic disease.

According to P. Wallen et al. (Prog. Chem. Fibrinolysis Thrombolysis 5, 16–23 (1981)) tPA occurs in two different forms, one being a single-chain form which is converted by plasmin or trypsin into two chains linked by disulphide bridges, and which those authors consider to be a degradation product of the former. The two-chain form is said to be fibrinolytically more efficient in fibrinolytic test systems (in vitro) than the one-chain form. Aprotinin is said to inhibit the conversion of the one-chain into the two-chain form so that theone-chain form may be recovered as the only or predominating form.

This work is referred to in more recent publication by Dingeman, Rijken, Hoylaerts and Collen (J. Biol. Chem., 257, 2920–2925 (1982), European patent application 0 041 766) who describe both forms as plasminogen activators, whose "plasminogen activating properties . . . are similar". They suggest that the one chain form when it is adsorbed on a fibrin clot is quickly converted to the two-chain form so that the fibrinolysis "occurs mainly via two-chain derivative". They conclude: "this conversion does not seem to play a role in the regulation of fibrinolysis". According to their findings the "two molecular forms had the same activity (lysistime.)", and "the catalytic efficiencies of both molecular forms are virtually identical therefore the one-chain form cannot be considered to be a less active precursor nor the two-chain form to be a less active degradation product". Whether or not the aforesaid conclusions are all correct, it is clear that both "molecular forms" have utility for therapeutic as well as in vitro fibrinolysis.

In actual fact, in the light of recent research results by the present inventors, it is clear that the above conclusions require some qualification. Pro-tPA is indeed in a sense a precursor of tPA, although not a totally inactive precursor. Its inherent activity is about one tenth that of tPA, so that on that basis alone it would at first sight appear preferable to administer tPA for therapeutic purposes rather than pro-tPA which first has to be converted into tPA before it can exercise its full therapeutic effect.

As a matter of fact, although European patent application 0041766 describes two compounds which presumably represent tPA as well as pro-tPA, only the former compound is actually characterized in respect of its fibrinolytic, fibrinogenolytic and thrombolytic effects. There is no such description for pro-tPA, nor any specific description of its use as a pharmaceutical composition. The claims for the pharmaceutical use of the compounds, to the extent that they are specific are directed only to the double-banded form, i.e., tPA. The only published actual therapeutic use of the substance has been the use in the double-stranded tPA form (Weimer et al., The Lancet, Nov. 7, 1981 p 1018–1020).

According to the aforesaid prior art, no method was known which lends itself readily to the manufacture of 2-chain tPA on a commercial scale, nor of the single-chain form herein referred to as "pro-tPA".

According to a recent proposal by the present inventors (RSA patent application 82/9168 and applications based thereon in other countries and which at present are not yet part of the state of the art) a process has been proposed which lends itself readily to such commercial scale manufacture.

SUMMARY OF THE INVENTION

It is an object of the present invention to provide a new and relatively simple process for the selective, reversible adsorption of tPA and/or pro-tPA from solutions, in particular for the manufacture of purified plasminogen activators.

It is a particular object of the invention to provide a new process for the manufacture optionally of purified tPA, purified pro-tPA and purified mixtures of tPA and pro-tPA. It is a further object to provide processes as aforesaid, capable of separating tPA and pro-tPA from urokinase and which if desired, can be adapted to the separate recovery of urokinase.

It is also an object to provide preparations comprising optionally tPA, pro-tPA, or mixtures of both.

In particular it is an object to provide a method of treatment and pharmaceutical preparations based on some not previously known properties and advantages of pro-tPA over tPA which can be put to beneficial use not only in the management of thrombosis and embolism, which have already occurred but also in the prophylaxis against such conditions.

It is yet a further object to provide a novel affinity reagent suitable for the above process and for the selective adsorption of tPA and/or pro-tPA.

Having regard to the aforegoing, the present invention, according to one aspect thereof provides a process for selectively and reversibly adsorbing tPA and/or pro-tPA from an aqueous medium containing such tPA and/or pro-tPA in solution which comprises intimately contacting the aqueous medium with an affinity reagent comprising an immobilized Kunitz type inhibitor of the type occurring in seeds of *Erythrina Latissima* and other Erythrina species and having the property of being an inhibitor for trypsin, plasmin and tPA but having no effect on urokinase, thereby selectively adsorbing the tPA and/or pro-tPA on the affinity reagent.

The process is primarily intended for the manufacture of purified plasminogen activators and precursors thereof, in particular tPA and/or its precursor pro-tPA, and also in appropriate cases urokinase. However, the process can be applied to all uses where it is desired or required to remove tPA and/or pro-tPA from aqueous solution, more particularly selectively, e.g., selectively against urokinase. This may include the selective removal of interfering amounts of tPA and/or pro-tPA from biological materials (optionally followed by the recovery of the tPA and/or pro-tPA in purified form), be it for scientific, analytical, diagnostic, pathological, therapeutic or preparative purposes.

The same process is of particular utility when adapted for the purification of tPA and/or pro-tPA. In that case the process comprises intimately contacting an aqueous medium containing dissolved tPA and/or pro-tPA and contaminants with the affinity reagent, thereby selectively adsorbing the tPA and/pro-tPA from the medium, removing the affinity reagent loaded with tPA and/or pro-tPA from contact with the aqueous medium and non-adsorbent contaminants, desorbing the tPA and/or pro-tPA from the affinity reagent and recovering the desorbed tPA and/or pro-tPA.

The seed of *Erythrina Latissima* (broad-leafed Erythrina) and other Erythrina species contains two proteinase inhibitors (Francois J Joubert et alia, Z. Physiol. Chem. 362 pages 531–538). They are referred to in that publication as DE-1 and DE-3. Whereas DE-1 inhibits bovine chymotrypsin and not bovine trypsin, DE-3 inhibits trypsin but not chymotrypsin. One of these, DE-3, has the property of being an enzyme inhibitor of the Kunitz type and of being an inhibitor for trypsin, plasmin and tPA, but having no effect on urokinase. DE-3 was selected after screening hundreds of enzyme inhibitors for being the only one capable of distinguishing between tPA and urokinase. It was found that if this inhibitor is immobilized, e.g., in manners known per se, it forms an affinity reagent which selectively extracts by adsorption tPA—as well as the previously unknown precursor of tPA, pro-tPA, while leaving the contaminants unadsorbed in the aqueous solution. Because DE-3 is an inhibitor for plasmin, it prevents the conversion of pro-tPA into tPA by the action of the plasmin which is normally present in aqueous liquids suitable as sources of tPA and/or pro-tPA. Accordingly, this immobilized inhibitor has outstanding properties when used as an adsorbent for pro-tPA. A more complete chemical characterization of DE-3 is contained in the above publication of Joubert el al.

Urokinase, if present in the aqueous solution, is not adsorbed. Accordingly, the affinity reagent can also be used in the process according to the invention when the tPA and/or pro-tPA is contaminated with urokinase and the urokinase is removed with the non-adsorbed contaminant. This means that the process can be applied to recover tPA from a large number of sources such as various kinds of tissue wherein tPA and/or pro-tPA occur in mixture with urokinase.

However, a particularly preferred aqueous liquid to be used for the extraction of tPA and/or pro-tPA therefrom is a harvest fluid, preferably serum-free, obtained from a tissue culture of human melanoma cells containing tPA and/or pro-tPA in the secretory products of the cells.

In accordance with preferred embodiments, the tPA and/or pro-tPA is adsorbed by passing the aqueous medium containing it through a bed of the affinity reagent, followed by washing the bed and subsequent desorption of the tPA and/or pro-tPA and washing the desorbed tPA and/or pro-tPA off the bed. The bed may for example be in the form of a column.

The desorption is preferably carried out with aqueous potassium thiocyanate solution preferably from about 1 to 3 molar, e.g., from 1.4 to 2 molar, preferably 1.6 molar at a pH at which tPA is stable, preferably dissolved in approximately neutral phosphate buffered saline, e.g., between 0.3 and 1.0 molar, preferably about 0.4 molar in respect of NaCl and preferably containing a stabilizing amount of a suitable surfactant, e.g., 0.1% Tritoh X-100 or Tween. The desorption may be carried out with chaotropic desorbents other than potassium thiocyanate. The desorption may also be carried out at low pH, e.g., from 2 to 3.5, preferably from 2.8 to 3. Other suitable desorbing conditions are high salt concentrations and/or the presence, of arginine and/or the presence of benzamidine. Such desorbing conditions are known as such to persons skilled in the art and therefore require no detailed description.

Also according to the invention, if it is desired to recover tPA free of pro-tPA, any pro-tPA, whether produced by the process steps described further above or not may be readily converted enzymatically into tPA, e.g., by exposing the pro-tPA in aqueous solution to the action of plasmin or enzymes having an equivalent effect on pro-tPA. Such an enzyme as yet unidentified occurs for example, in fibrin for which reason the conversion of pro-tPA into tPA also occurs in the presence of fibrin. Kallikrein also produces this effect, albeit less effectively.

It has now been found that pro-tPA as produced in accordance with the present invention differs from tPA in that the former is a single-chain compound which has only slight plasminogen activator properties, whereas tPA (molecular weight 72,000 dalton) is a double-chain compound and has pronounced plasminogen activator properties, about 10 times as strong as pro-tPA. Pro-tPA has the same molecular weight as tPA.

Because of this weak activity in the single-chain form and the knowledge that double-chain tPA is so much more active the prior art would normally have created a strong incentive to employ the plasminogen activator in pharmaceutical compositions in the tPA form (i.e., the double-stranded molecular form), because in vivo it is the tPA form which is predominantly effective in the clot dissolving process. This view is reinforced by the knowledge that pro-tPA itself is very weakly active.

However, surprisingly it has now been established by experimental evidence that there are convincing reasons for using the plasminogen activator in the pro-tPA form, preferably at least predominantly so but better entirely so, rather than using tPA as the active ingredient of pharmaceutical compositions for the management of thrombotic disease or other forms of therapy wherein use is made of the fibrinolytic effect of the plasminogen activator. The reason for this is that the pro-tPA has a higher affinity for adsorption to fibrin than the tPA form and that once it has been adsorbed by fibrin it is converted very rapidly into tPA and then acquires the full desired activity, exactly where it is needed, namely at the clot. The consequences to be concluded from this finding are:

(a) that pro-tPA will be absorbed more rapidly and completely at a clotted fibrin site, that is where the substance is actually needed. There the pro-tPA is rapidly converted—in situ—into tPA by the proteolytic enzymes present in the fibrin whereupon the full plasminogen activating activity of tPA becomes available immediately at the actual site of the clot.

(b) Pro-tPA will be more selective than tPA for bringing about fibrinolysis because it is relatively inactive until it attaches to the fibrin and only becomes fully active by its conversion into tPA in situ. With tPA there exists an about 10 times greater probability that it may activate some plasminogen in the bloodstream instead of at the thrombus where the fibrinolytic effect is required. This relative probability is even further increased by the lower affinity of the tPA form for adsorption to the fibrin site.

(c) Because of the drastically reduced activity while in the bloodstream, it can now be recommended with confidence to employ pro-tPA in prophylactic therapy, where there is a risk of future thrombotic or embolic occurrences.

(d) On the other hand the risk of side effects when using relatively high dosages in acute cases of thrombotic occlusions is also diminished.

(e) tPA has a short halflife in vivo. The properties of pro-tPA are such as to render the utilisation of the plasminogen activator more efficient On the one hand pro-tPA is less likely to be consumed by ineffective reactions while still in the bloodstream. On the other hand, it is more likely to be "captured" rapidly by the clot site, where it can be effective.

Based on the above important concept, the present invention also provides a method of fibrinolytic treatment for the management or prophylaxis of thrombosis, embolism or other conditions where it is desired to produce fibrinolytic or proteolytic activity via the mechanism of plasminogen activation, which comprises administering intravenously to a patient a plasminogen activator composition comprising a plasminogen activator component represented by the tPA/pro-tPA couple and composed of from 50 to 100% pro-tPA and from 0 to 50% tPA at a dosage rate designed to produce, in the blood-stream, an average plasminogen activator activity of less than half, e.g., between 5 and 30% that which results from the administration of up to 15 mg per 24 hours of tPA.

Preferably the dosage of tPA/pro-tPA couple is up to about 15 g per 24 hours. Also preferably the tPA/pro-tPA couple is represented by 70 to 100% pro-tPA and 0 to 30% tPA, more preferably by 80 to 100% pro-tPA and 0 to 20% tPA.

It is preferred (and readily possible because of the low activity of pro-tPA in therapeutically effective dosages) for the plasminogen activator activity in the bloodstream to be maintained at less than 20% that which results from the administration of 15 mg per 24 hours of tPA.

The method may be applied to the management of thrombosis or embolism where thrombotic occlusion has already occurred and then comprises intravenously administering to the patient from 3 to 15 mg per 24 hours of the tPA/pro-tPA couple. This may be done in dosage units of 3 to 15 mg of tPA/pro-tPA couple. It may also be done by intravenous infusion at a rate of ⅛ to ⅝ mg per hour of tPA/pro-tPA couple.

The invention is also particularly applicable to the prophylaxis of conditions involving thrombotic occlusion comprising the intravenous administration to the patient of dosage units of from 1 to 10 mg of tPA/pro-tPA couple or the intravenous infusion of the plasminogen activator composition at a rate of 0.5 to 2 mg per hour of tPA/pro-tPA couple. Such prophylactic treatment may be administered to a patient showing no symptoms of thrombosis or embolisation at all but who is, nevertheless, at risk. Examples are bedridden patients or debilitated patients who, by virtue of venous stasis are particularly liable to suffer deep vein thrombosis and embolisation. Other examples are patients with unstable angina in whom thrombotic coronary artery occlusion is likely to be imminent. Further examples are patients with cardiac valvular disease in which thrombine is situated in the legions and where there is a risk of cerebral embolisation. Examples are patients where the cavities of the heart or the great blood vessels have lesions or damage such that a risk exists of blood clots becoming dislodged and causing cerebral vascular occlusion (strokes). Examples are also patients with prosthetic vascular valves and atrial fibrilation, sub-acute bacterial endocarditis etc. The method is also useful for the prophylactic treatment of patients receiving intravenous therapy or total parentheral nutrition, where the venous line is inserted into a large vein and where irritant solutions are infused, likely to cause venous thrombosis and occlusion and/or embolism.

While continuous intravenous infusion is preferred for the administration, intermittent pulsed intravenous administration may be applied as well in the above dosages of e.g., 1 to 10 mg, say every 2 to 24 hours.

In the light of the aforegoing, the invention also provides a pharmaceutical composition for the management or prophylaxis of thrombosis, embolism or other conditions where it is desired to produce local fibrinolytic or proteolytic activity via the mechanism of plasminogen activation which comprises a plasminogen activator component presented by the tPA/pro-tPA couple composed by 50 to 100% pro-tPA and 0 to 50% tPA, the composition being adapted for intravenous administration in dosage units of up to 15 mg of tPA/pro-tPA couple or by intravenous infusion at an infusion rate of up to 15 mg per 24 hours of tPA/pro-tPA couple and adapted to produce, in the bloodstream, an average plasminogen activator activity of less than half, preferably between 5 and 30%, e.g., less than 20% of that which results from the administration of up to 15 mg per 24 hours of tPA. As for the remainder what has been stated above in connection with the method of treatment applies mutatis mutatis to the pharmaceutical composition.

The present invention allows the preparation of purified tPA or pro-tPA separately or as a mixture.

The present invention also permits the recovery of pro-tPA from an aqueous medium containing it and also containing plasmin and/or plasminogen and a plasminogen activator. This requires inhibiting plasmin in the aqueous medium and removing the pro-tPA from the aqueous medium while plasmin is inhibited. In this context it is pointed out that tPA, when present acts as a plasminogen activator causing plasmin to be formed, which in turn must be inhibited.

In the above-described process, according to the invention, the pro-tPA is adsorbed from the aqueous medium by an affinity reagent comprising an immobilized inhibitor for plasmin as well as having an affinity for pro-tPA, from which pro-tPA is subsequently desorbed and recovered in purified form. The pro-tPA thus recovered may then be sterilized and stabilised with a physiologically compatible stabiliser in the form of an intravenously injectable aqueous solution.

Because the DE-3 inhibitor which according to the invention is used in its immobilized form as an affinity reagent happens to be an inhibitor of plasmin and because plasmin is normally present in the media from which the tPA and pro-tPA is to be recovered and has the property of converting pro-tPA into tPA, the use of this inhibitor to isolate pro-tPA simultaneously serves to preserve the pro-tPA in its pro-tPA form.

According to a further aspect of the present invention, it is possible to selectively adsorb tPA and/or pro-tPA separately from and in addition to urokinase from aqueous media containing both plasminogen activators (as such or as a precursor). This may be applied to the manufacture of either purified tPA and/or pro-tPA free of urokinase on the one hand or of purified urokinose free of tPA and pro-tPA on the other hand or of both purified types of plasminogen activators. This can be done by contacting such an aqueous medium with an affinity reagent comprising an immobilized Kunitz type inhibitor of the type occurring in seeds of *Erythrina latissima* and other Erythrina species and having the property of being an inhibitor for trypsin, plasmin and tPA, but having no effect on urokinase, thereby selectively adsorbing the tPA and/or pro-tPA from the solution, removing the affinity reagent loaded with tPA and/or pro-tPA from contact with the aqueous medium depleted of tPA and/or pro-tPA, but still containing the urokinase, and recovering urokinase from the aquous medium depleted of tPA and/or pro-tPA. Suitable aqueous media for this process will be aqueous extracts of random mammalian tissue cells or media containing the secretion products of such cells since such media contain both plasminogen activators. Once again, the adsorbed tPA and/or pro-tPA may be desorbed and recovered, and if desired pro-tPA may be converted into tPA either before or after the adsorption on the selective affinity reagent.

The urokinase may be recovered from the aqueous medium in any suitable manner, for example by being adsorbed from the aqueous medium using an affinity reagent having an affinity for urokinase. Such affinity reagents may be immobilized inhibitors having no selectivity for tPA over urokinase. It is also possible to use as an affinity reagent antibodies against urokinase,suitably immobilized in a manner known per se.

Also, in accordance with the invention, there is provided a new affinity reagent which comprises a Kunitz-type inhibitor of the type occurring in seeds of *Erythrina latissima* and other Erythrina species and having the property of being an inhibitor for trypsin, plasmin and tPA, but having no effect on urokinase, immobilized by being bonded to a solid carrier, e.g., by being covalently bonded to the carrier. For example, the inhibitor may be coupled to cyanogen bromide activated agarose in a manner known as such to persons skilled in-the art. However, other solid carriers can be used and other coupling agents depending on the chemical properties of the surface to which the inhibitor is to be coupled. Examples are, (a) carbodialmide coupling which couples free amino groups to free carboxy groups;

(b) glutaraldehyde coupling which couples $NH_2$ groups to agarose previously converted into the amino-alkyl form;

(c) periodate activation of agarose to generate aldehyde functions which are subsequently reacted at pH 4 to 6 with amines of the inhibitor to form Schiff bases which are then reduced with sodium borohydride or sodium cyano borohydride;

(d) the agarose may be converted into the hydrazidosuccinyl derivative; to this carboxylic ligands may be attached with EDC, or amines by diazotisation;

(e) cellulose fibres or beads may be converted into a hydrazide derivative and used according to the method of Parikh et alia (Methods in enzymology Vol. 34, pages 77 to 102, editors W B Jakobi and Wilcheck, Academic Press N.Y.).

(f) polyacrylamide beads may be coupled by direct glutaraldehyde procedure or by diazotisation of the p-aminobenzamido ethyl derivatives or of the hydrazido derivative;

(g) proteins, e.g., albumin or trypsin or gelatin may be coupled, e.g., in the form of hydrazides;

(h) finally, reference is made to glass beads (or other solid bodies) which can be coated with a protein, e.g., gelatin which may be cross linked and coupled to the inhibitor by methods analogous to any of the coupling methods described in RSA patent application No. 81/4481, and corresponding applications abroad (German patent application P 3224837.7, Japanese patent application 116086/1982, United Kingdom patent application 8219070 and U.S. patent application 392111).

The aforegoing methods are known as such to persons skilled in the art and/or are described in the cited literature and require no detailed description.

The scope of the invention includes a process for making an affinity reagent which comprises covalently bonding to a solid carrier a Kunitz-type inhibitor of the type defined further above, e.g., by any of the procedures set out above.

The affinity reagent according to the invention may be used for the manufacture of tPA and/or pro-tPA and of preparations comprising tPA and/or pro-tPA, e.g., in the processes as set out further above. However, the affinity reagent can also have utility as a diagnostic or analytical reagent.

The scope of the invention extends to pro-tPA as such purified according to the invention as well as to a purified mixture of tPA and pro-tPA and more particularly such a mixture wherein the ratio of pro-tPA to tPA exceeds 1:2 and may even exceed 1:1.

In order to produce even higher ratios, e.g., as high as 9:1 or more, it is proposed to produce the pro-tPA by cultivation of pro-tPA-yielding cell cultures, e.g., melanoma cells in a suitable culture medium, either in the absence of enzymes which catalyse the conversion of pro-tPA to tPA or in a medium containing such enzymes, e.g., containing serum, and suitable inhibitors adapted to inhibit such enzymes (more particularly plasmin) which catalyse the conversion of pro-tPA to tPA. Suitable inhibitors are Soyabean-derived trypsin inhibitors or alpha 1-antiplasmin. Aprotinin can be used instead (as is already known). The pro-tPA is then recovered from the medium in the absence of said enzymes or in the presence of the inhibitor(s).

If a mixture of pro-tPA and tPA is available and if it is desired to restrict the enzymatic activity thereof to that of pro-tPA, it is possible to remove the tPA by using an inhibitor which irreversibly inhibits tPA. A suitable example thereof is the irreversible proteinase inhibitor diisopropyl phosphofluoridate. The inhibitor may subsequently be removed by dialysis or gel chromatography. The irreversibly inhibited tPA may be left in the mixture.

The scope of the invention extends to pharmaceutical compositions comprising tPA and/or pro-tPA prepared or purified by a process according to the present invention dissolved in a physiologically compatible injection medium. The scope of the invention also includes fibrinolytic preparations for carrying out fibrinolysis in vitro, e.g., for diagnostic or pathological or general scientific purposes.

It is considered an advantage of the invention that it can be adapted substantially at will to produce compositions as aforesaid comprising optionally tPA or pro-tPA as the only active ingredient or tPA and pro-tPA in a desired ratio.

The scope of the invention includes a method of local fibrinolysis or proteolysis by the action of plasmin which comprises liberating the plasmin locally from plasminogen by plasminogen activation with tPA which in turn is formed locally from pro-tPA produced as herein described.

EXAMPLES

The invention will now be described by way of example, more particularly by way of the following non-limiting embodiment(s), which, if read in the context of the aforegoing general description, will enable the person skilled in the art to practise the full scope of the invention.

Example 1

Preparation of Affinity Reagent According to the Invention DE-3 Inhibitor is Prepared as Follows:

*Erythrina latissima* seeds are collected and processed according to the method of Joubert et al. The seeds are ground, defatted and extracted at 10° C. overnight with 0.5 molar sodium chloride solution. The extract is centrifuged and DE-3 inhibitor is recovered from the supernatant by ammonium sulphate precipitation followed by chromatography on Sephadex G50, DEAE cellulose and DEAE sepharose. The finally purified material migrates as a single band with an apparent molecular weight of 22,000 daltons when subjected to electrophoresis on a 15% polyacrylamide gel containing 0.1% sodium dodecyl sulphate (SDS).

Purified DE-3 (26 mg) is coupled to 5 ml of commercially available cyanogen bromide activated agarose in the usual manner (Sepharose 4B marketed by Pharmacia and who also supply the instructions for the use of the preparation). The affinity reagent was equilibrated against phosphate buffered saline of pH 7.4 containing 0.4 M sodium chloride, 0.1% Triton X-100 (a commercial detergent commonly used in this art) and 0.02% sodium azideas a stabiliser. This affinity reagent is then packed into a 5 ml column fashioned from the barrel of a disposable plastics syringe.

Example 2

Preparation and Purification of tPA and Pro-tPA

A medium containing tPA and pro-tPA is produced as follows: Human melanoma cell of a cell line known as Bowes cells RPMI-7272 (obtained from Denver Hospital, Denver, Colo. and described in J.Biol.Chem. 256, 7035–7041) are grown as adherent monolayers in RPMI 1640 tissue culture medium supplemented with 10% heat inactivated (56° C.; 30 minutes) foetal bovine serum (FCS) and antibiotics (300 $\mu$g per ml penicilin; 200 $\mu$g per ml streptomycin and 10 $\mu$g per ml of tylocine). The cells are passaged at confluence (approximately 4×10$^5$ cells per cm$^2$) by trypsinisation and reseeding at 5×10$^5$ cells per 100 mm. dish. After aspirating the medium, the cells are incubated in 0.25% trypsin in tris dulbecco's saline (24.8 mM tris HCl pH 7.4 containing 0.1 mM Na$_2$HPO$_4$, 5 mM KCl, 0.14 M NaCl) at 37° C. for 5 minutes. Detached cells are dispersed by gentle pipetting and the suspension is added to an equal volume of medium containing foetal bovine serum to'neutralise the protease. The cells are then washed by centrifugation at 350 g for 5 minutes, resuspended and reseeded into fresh dishes.

From these stock cultures the cells are grown as adherent monolayers in 75 cm$^2$ or 150 cm$^2$ tissue culture flasks and allowed to grow to near confluency in mediums supplemented with 10% foetal bovine serum. The cultures are then washed once and covered with 20 ml of serum-free medium. After 24 hours the medium is collected and fresh medium is added.

The harvest fluids are centrifuged at 2000 rpm for 5 minutes to remove whole cells and cellular debris. The solution is stabilised with Triton X100 (0.1%) or Tween 80 (0.1%) and acidified with glacial acetic acid (pH 5.5 to 6.0) for storage at −20° C.

2l of harvest fluid are made 0.4 molar with respect to NaCl and are filtered through a 0.45 μm membrane. The filter harvest fluid is then applied to the affinity column at a flow rate of 45 ml/hour at room temperature. The effluent is collected at 4° C. and monitored for the presence of plasminogen-dependent fibrinolytic activity. No tPA or pro-tPA is detected.

After the total volume of harvest fluid has passed through, the column is washed with 6 column volumes of phosphate buffered saline containing 0.4 M NaCl and 0.1% Triton X-100. No tPA or pro-tPA is eluted by this procedure.

Adsorbed proteins are then eluted using PBS containing 1.6 M potassium thiocyanate, 0.4 M NaCl and 0.1% Triton X-100.

The protein content is monitored by reading the absorbance at 280 nm. All plasminogen-dependent fibrinolytic activity is found to be eluted as a sharp peak when potassium thiocyanate is added to the eluting buffer, and this peak corresponds to a small protein peak.

The fractions containing the highest activity are pooled to give 6 to 8 ml solution stored at −20° C. and which represents 70 to 80% of the activity applied to the column. Fractions containing low activity are pooled separately. The total recovery of activity in both pools usually amounts to 90 to 100%. The potassium thiocyanate eluate contains a single band of protein with a molecular weight of 72,000 daltons corresponding to a mixture of pure tPA and pro-tPA, the latter in different runs amounting to from 39 to about 50% of the total or more.

The yields improve if the same column is used repeatedly over and over again. The column thus not only remains effective to be re-used many times, but in fact improves with use. This is surprising because tPA has the property of cleaving the inhibitor DE-3 when in its non-immobilized form.

Example 3
Pharmaceutical Preparation Containing tPA and/or Pro-tPA

The pooled fraction containing tPA and/or pro-tPA are dialysed against 0.30 molar sodium chloride containing 0.01 volume percent Tween 80 and stored at −80° C. Prior to administration the concentration is adjusted to 75 μg per ml of tPA plus pro-tPA (for therapeutic purposes the dosage rate for tPA is the same as for pro-tPA) and 0.3 molar NaCl. The solution is sterilized by filtration through an 0.22 μm membrane filter.

The solution is administered intravenously by infusion at a dosage rate of between 3 and 15 mg per 24 hours, typically, 7.5 mg per 24 hours. Ideally the dosage rate should be such that during the treatment the total plasminogen activator (including precursor) level in the blood rises to between 0.6 and 1, preferably about 0.8 international units per ml. At such concentrations the treatment is found to be highly effective for clearing thrombosis and no systemic fibrinolysis is observed.

However, because pro-tPA is only converted to tPA after binding to fibrin has occurred, the actual activity while still in the blood stream is found to be a small fraction, as little as 10% of that which would be present if all the plasminogen activator were to be in the fully active tPA form. Because moreover pro-tPA is more quickly and more strongly adsorbed by fibrin than is tPA. The reaction of promiscuous reactions is reduced even further.

Example 4
Mass Cultivation of Melanoma Cells

A spinner flask charged with Rosswell Park Memorial Institute culture medium 1640/10% foetal bovine serum is inoculated with melanoma cells at a concentration of $5\times10^5$ cells per ml. The flask is kept at 37° C. and stirred magnetically at 30 rpm. Medium is pumped out of the flask at a rate of 1% the volume of the flask per hour and replaced at the same rate with fresh medium which has been equilibrated with 5% $CO_2$ in air. The cells are retained in the culture vessel by an outlet glass tube plugged with glass wool. The withdrawn medium is filtered through a millipore filter.

The collected liquid is pasteurised and can now be processed according to Example 2.

Example 5
Cultivation of Melanoma Cells for High Pro-tPA Yields

Example 2 is modified by the addition to the culture medium of sufficient soybean trypsin inhibitor or alpha-1-anti-plasmin to inhibit the serum plasmin. In all other respects the process is carried out as in Example 2, the ratio of pro-tPA to tPA in the final product being now increased to approximately 9:1. The experimental details were as follows:

The Bowes cell culture medium contained 0.1% triton and 10 KIU trasylol (plasmin inhibitor). The initial harvesting fluid had a volume of 1960 ml. The KSCN eluate had a volume of 20.8 ml. The recovery of tPA +pro-tPA was 100% of which 87% was in the pro-tPA form.

In a comparative experiment carried out without trasylol the recovery was 98%, composed entirely of tPA and no detectable pro-tPA.

Example 6
Elimination of Residual tPA in Mixtures of Pro-tPA and tPA

The solution of tPA and pro-tPA is rendered 10 mM with respect to diisopropyl phosphofluoridate. The pH is adjusted to 8. After 4 hours the tPA has been permanently inhibited. The residual inhibitor is thereafter removed by dialysis.

Example 7
Conversion of pro-tPA into tPA

An aqueous solution containing 100 μg of protein/per ml is mixed with an equal volume of phosphate buffered saline containing 5 μg/per ml of plasmin and is incubated for 16 hours at 20° C. Sodium dodecyl sulphate is added to a final concentration of 0.1% and the proteins are precipitated with 6% trichloracetic acid. The precipitate is washed in acetone and redissolved in 0.06 M Tris HCl pH 6.8 containing 1sodium dodecyl sulphate and 10% glycerol.

After this treatment, it can be shown by electrophoresis that the pro-tPA has been converted completely into the active tPA form.

Example 8
The Selectivity of Pro-tPA for Insolubilised Fibrin

Samples of tPA/pro-tPA couple containing different percentages of pro-tPA (the balance being tPA were tested under identical conditions to establish the relative proportions of substance bound to a sample of fibrin in each case.

The percentages of pro-tPA in the sample (the balance being tPA were determined by measuring the fibrinolytic activities of the samples before and after treatment with plasmin (in order to convert pro-tPA into tPA). Thereafter a 10% correction factor was applied to compensate for the fact that pro-tPA has 10% of the fibrinolytic activity of tPA. The samples were then diluted in 0.1 molar tris HCl, pH 8.1, containing 0.1% Triton-X-100 so that 0.2 ml would in the presence of micrograms of plasminogen release approximately 30 to 50% of fibrin, labelled with iodine 125 isotope coated on the bottom of limbro wells in the course of one hour. Aliquots (0.2 ml) were added to limbro wells coated with the radioactive iodine-labelled fibrin in quadruplicate. After incubation for one hour at 0° C. two wells of each quadruplicate set were treated three times with the Tris HCl to remove unbound tPA. Thereafter, the bound activity was determined. These results were compared with results obtained on wells that had not been washed. The results are summarized in the following table.

| % activity | Fibrinolytic activity pro-tPA (corrected) | Total activity | C % $^{125}$I-fibrin solubilised in 60 min) Activity after wash | % bound |
|---|---|---|---|---|
| 88.7 | 97.6 | 29.83 | 29.48 | 98.8 |
| 34.0 | 37.4 | 45.90 | 37.52 | 81.7 |
| 64.0 | 70.4 | 56.56 | 41.53 | 73.4 |
| 87.0 | 95.7 | 48.88 | 48.76 | 99.8 |
| 88.0 | 96.8 | 53.85 | 52.49 | 97.5 |

The results demonstrate that pro-tPA is substantially more completely bound by the fibrin than tPA.

Example 9

Prophylactic Treatment

Prophylactic treatment is given to patients for whom a substantial risk of thrombosis or embolisation exists (note: the treatment is contra-indicated for post operative treatment or immediately post partem) suitable patients include bed-ridden or debilitated patients who, by virtue of venous stasis are prone to deep vein thrombosis and embolisation, patients with unstable angina in whom thrombotic coronary artery occlusion is thought to be imminent, patients with diseased heart cavities or great blood vessels, prosthetic vascular valves, atrial fibrilation, sub-acute bacterial endocarditis, patients receiving intravenous treatment with irritant solutions.

For this kind of treatment the dosage rate is 1 to 10 mg by intermittent pulse intravenous administration once every 2 to 24 hours. For this purpose ampoules are made up containing the desired amount of from 1 to 10 mg dissolved in 5 ml 0.30 molar saline containing 0.01 volume percent Tween 80 and optionally conventional concentrations of stabilisers such as albumin or mannitol.

Infusion solutions are made up in the same medium in concentrations designed for an administration rate of 0.5–2 mg per hour of pro-tPA/tPA couple.

A typical such solution would contain between 4 mg per liter (lower range)and up to 16 mg per liter (higher range) or 8 mg per liter (average).

Example 10

It was determined that the plasminogen activating activity of pro-tPA is not zero as in most enzyme precursors, but that it amounts to 10% that which is obtained after complete conversion into double-chain tPA.

The effect is that the administration of tpA/pro-tPA couple comprising 50–100% pro-tPA and 0–50% tPA (even at the time of injection when the concentrations are highest, having regard to the half life of the substances in vivo) results in a much lower activity in the bloodstream than would arise from the administration from an equivalent amount of tPA. This will be understood from the following table:

| percentage | | | % activity in dosage |
|---|---|---|---|
| tPA % | pro-tPA % | dosage | compared with 15 mg pure TPA |
| 50 | 50 | 4 mg | 14.7% |
| | | 8 mg | 29.3% |
| | | 10 mg | 36.7% |
| | | 13 mg | 47.79% |
| 30 | 70 | 4 mg | 8.7% |
| | | 8 mg | 19.7% |
| | | 15 mg | 37% |
| 20 | 80 | 4 mg | 7.5% |
| | | 8 mg | 14.9% |
| | | 15 mg | 28% |
| | | 20 mg | 37.3% |
| | | 25 mg | 46.7% |
| 0 | 100 | 4 mg | 2.6% |
| | | 15 mg | 10% |
| | | 25 mg | 16.7% |
| | | 50 mg | 33.3% |

The above table demonstrates the reduced probability of promiscuous plasminogen activation in the bloodstream resulting only from the newly discovered fact that pro-tPA has only 10% the activity of tPA. Added to this is the newly discovered effect of pro-tPA being adsorbed more selectivity (i.e., rapidly and strongly) from the bloodstream as soon as it reaches a fibrin site (see Example 8).

I claim:

1. A pharmaceutical composition suitable for the treatment or prophylaxis of thrombosis or embolism which composition acts selectively in the presence of fibrin by means of local plasminogen activation and which is in dosage units for injection or intravenous infusion, said composition comprising:

(a) a human tPA/human pro-tPA couple composed of 70–100% human pro-tPA and up to 30% human tPA; and (b) a physiologically compatible medium.

2. The composition according to claim 1, wherein the tPA/pro-tPA couple is 80–100% pro-tPA and 0–20% tPA.

3. The composition according to claim 1, wherein the tPA/pro-tPA couple is essentially pure pro-tPA.

4. The composition according to claim 1 for the management of thrombosis or embolism in intravenous dosage units of from 3 to 15 mg of tPA/pro-tPA couple or in the form of an intravenous infusion solution sufficient to provide an infusion rate of ⅛ to ⅝ mg per hour of tPA/pro-tPA couple.

5. The composition according to claim 1 for the prophylaxis of conditions likely to result in thrombosis or embolism in dosage units for intravenous administrations of 1 to 10 mg of tPA/pro-tPA couple or in the form of an infusion solution sufficient to provide an infusion rate of 0.5 to 2 mg per hour of tPA/pro-tPA couple.

6. The composition according to claim 1 wherein the amount of the tPA/pro-tPA couple is sufficient to produce in the bloodstream an average plasminogen activator activity of between 5 and 30% of that which results from the administration of up to 15 mg per 24 hours of tPA.

7. The composition of claim 1, wherein the amount of the tPA/pro-tPA couple in said dosage units is sufficient to provide an average plasminogen activator activity in the bloodstream of less than half of that which results from the administration of 15 mg per 24 hours of tPA.

8. A method of treatment or prophylaxis of thrombosis, embolism or other conditions where it is desired to produce fibrinolytic or proteolytic activity selectively in the presence of fibrin via the mechanism of plasminogen activation which comprises administering by injection or intravenously to a patient a plasminogen activator composition comprising a plasminogen activator component, said component being a human tPA/human pro-tPA couple composed of from 70 to 100% human pro-tPA and from 0 to 30% human tPA and a pharmaceutically acceptable carrier.

9. The method according to claim 8, wherein the total dosage of the tPA/pro-tPA couple is up to 15 g per 24 hours.

10. The method according to claim 8, wherein the tPA/pro-tPA couple is 80 to 100% pro-tPA and 0 to 20% tPA.

11. The method according to claim 8, wherein the plasminogen activator activity in the bloodstream is maintained at 5 to 30% of that which results from the administration of 15 mg per 24 hours of tPA.

12. The method according to claim 8, wherein the plasminogen activator activity in the bloodstream is less than 20% of that which results from the administration of 15 mg per 24 hours of tPA.

13. The method according to claim 8 for the treatment of thrombosis or embolism where thrombotic occlusion has already occurred and which comprises intravenously administering to the patient from 3 to 15 mg per 24 hours of the tPA/pro-tPA couple.

14. The method according to claim 13, wherein the intravenous administration is administered in dosage units of 3 to 15 mg of tPA/pro-tPA couple.

15. The method according to claim 13, wherein the administration proceeds by intravenous infusion at a rate of ⅛ to ⅝ mg per hour of tPA/pro-tPA couple.

16. The method according to claim 8 for the prophylaxis of conditions involving thrombotic occlusion, comprising intravenously administering to the patient dosage units of from 1 to 10 mg of the tPA/pro-tPA couple or intravenously infusing the plasminogen activator composition at a rate of 0.5 to 2 mg per hour of tPA/pro-tPA couple.

17. The method according to claim 16, wherein the patient is bed-ridden or debilitated and by virtue of venous stasis is at increased risk to suffer deep vein thrombosis or embolisation.

18. The method according to claim 16, wherein the patient suffers from unstable angina and in whom thrombotic coronary artery occlusion is likely to be imminent.

19. The method according to claim 16, wherein the patient suffers from cardiac valvular disease involving thrombin situated in lesions and a risk of cerebral embolisation.

20. The method according to claim 16, wherein the patient's cavity of the heart or great blood vessels have lesions or damage such that a risk exists of blood clots becoming dislodged and causing cerebral vascular occlusion.

21. The method according to claim 16, wherein the patient is receiving intravenous therapy or total parentheral nutrition, where the venous line is inserted into a large vein and where irritant solutions are infused, likely to cause venous thrombosis and occlusion and/or embolism.

22. The method according to claimed 8, wherein the plasminogen activator composition is administered at a dosage rate sufficient to produce in the bloodstream an average plasminogen activator activity of less than half of that which results from the administration of up to 15 mg per 24 hours of tPA.

23. The method according to claim 1, wherein the tPA/pro-tPA couple is essentially pure pro-tPA.

* * * * *